US00PP31462P3

(12) United States Plant Patent
van Langen

(10) Patent No.: US PP31,462 P3
(45) Date of Patent: Feb. 18, 2020

(54) *SEDEVERIA* PLANT NAMED 'TSAECH1802'

(50) Latin Name: x*Sedeveria*
Varietal Denomination: TSAECH1802

(71) Applicant: Tosjami B.V., Heerhugowaard (NL)

(72) Inventor: Gerard van Langen, Heerhugowaard (NL)

(73) Assignee: Tosjami B.V., Heerhugowaard (NL)

( * ) Notice: Subject to any disclaimer, the term of this patent is extended or adjusted under 35 U.S.C. 154(b) by 0 days.

(21) Appl. No.: 16/501,050

(22) Filed: Feb. 13, 2019

(65) Prior Publication Data

US 2019/0281748 P1 Sep. 12, 2019

(30) Foreign Application Priority Data

Mar. 6, 2018 (QZ) ..... PBR 2018/0660

(51) Int. Cl.
*A01H 5/12* (2018.01)
*A01H 6/00* (2018.01)
*A01H 6/32* (2018.01)

(52) U.S. Cl.
USPC ..... Plt./373
CPC ..... *A01H 6/00* (2018.05); *A01H 5/12* (2013.01); *A01H 6/32* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — Samuel R. McCoy, Jr.

(57) ABSTRACT

A new and distinct x*Sedeveria* plant named 'TSAECH1802' which is characterized by a relatively small and compact rosette of foliage born on a strong, short stem, and glaucous greyed-green foliage which exhibits a slight bluish hue that is lighter at the center of the rosette and progressively darker towards the outer whorls of foliage, as well as the stability of these characteristics from generation to generation.

4 Drawing Sheets

Latin name of the genus and species: The Latin name of the genus and species of the novel variety disclosed herein is *Echeveria elegans* x *Sedum morganianum* which is also known by the nothogenus, x*Sedeveria*.

Variety denomination: The inventive variety of x*Sedeveria* disclosed herein has been given the variety denomination 'TSAECH1802'.

CROSS REFERENCE TO RELATED APPLICATIONS

This application claims priority to the Community Plant Variety Rights application number 2018/0660, filed Mar. 6, 2018, which is herein incorporated by reference.

BACKGROUND OF THE INVENTION

Parentage: 'TSAECH1802' is an intergeneric hybrid seedling selection resulting from the controlled pollination of an unnamed *Echeveria elegans* plant (not patented), the seed parent, with an unnamed *Sedum morganianum* plant (not patented), the pollen parent. The crossing was made by the inventor in the spring of 2015 at a commercial greenhouse in Heerhugowaard, the Netherlands. In the autumn of 2016, one seedling from said cross of 2015 was observed to exhibit unique growth and foliage characteristics. The seedling was isolated for further evaluation in order to confirm the distinctness and stability of the characteristics first observed. Upon confirmation of distinctness and stability, 'TSAECH1802' was selected for commercialization.

Asexual Reproduction: Asexual reproduction of the new cultivar 'TSAECH1802', by way of rooting leaf cuttings, was first initiated in the summer of 2017 at the inventor's commercial greenhouse in Heerhugowaard, the Netherlands.

Through two subsequent generations, the unique features of this cultivar have proven to be stable and true to type.

SUMMARY OF THE INVENTION

The cultivar 'TSAECH1802' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TSAECH1802'. These characteristics in combination distinguish 'TSAECH1802' as a new and distinct x*Sedeveria* cultivar:

1. 'TSAECH1802' exhibits a small, compact rosette with an abundance of succulent foliage, which forms a short, strong stem with age; and
2. 'TSAECH1802' exhibits strong elliptic foliage which is slightly concave and slightly curved upward; and
3. 'TSAECH1802' exhibits glaucous greyed-green foliage with a slight bluish hue, which is lighter at the center of the rosette and becoming progressively darker towards the outer whorls of foliage.

BOTANICAL DESCRIPTION OF THE PLANT

Figure 1:
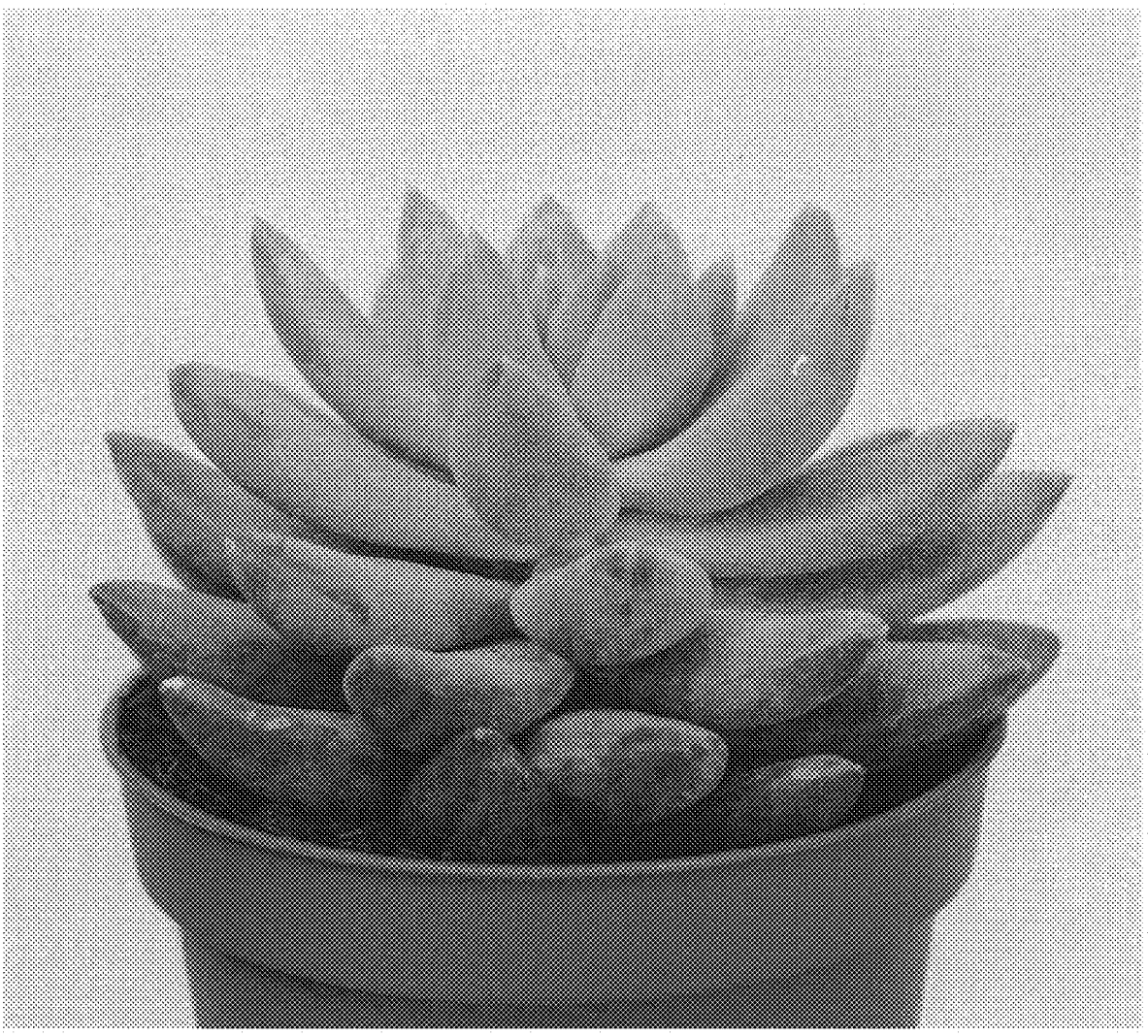
FIG. 1 illustrates, as nearly true as it is reasonably possible to make the same in color photographs of this type, an exemplary plant of 'TSAECH1802' grown in a commercial greenhouse in Heerhugowaard, the Netherlands. This plant is approximately 6 months old, shown planted in a 6 cm container.
Figure 2:
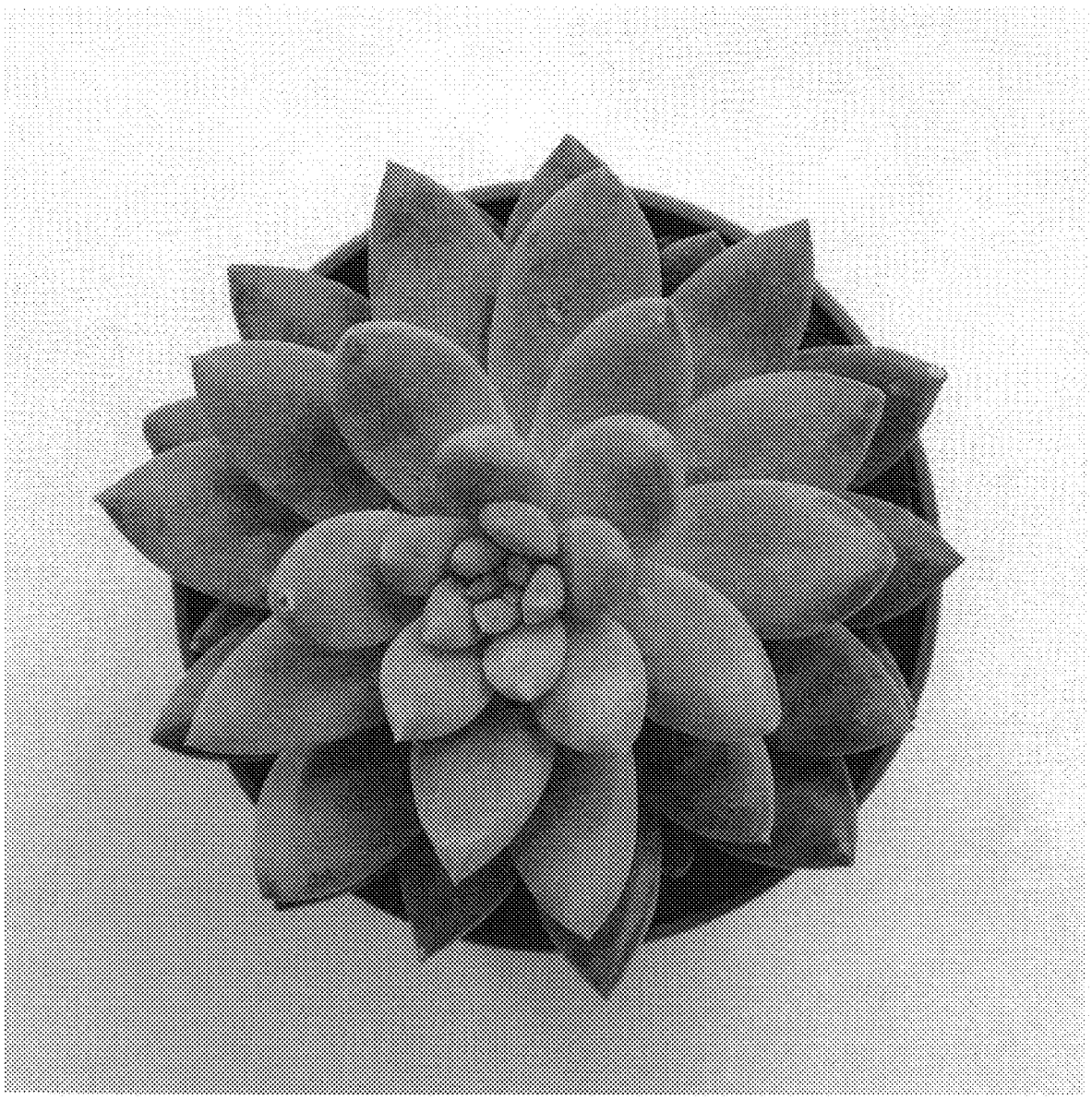
FIG. 2 illustrates, as nearly true as it is reasonably possible to make the same in color photographs of this type, the typical foliage arrangement of 'TSAECH1802.
Figure 3:
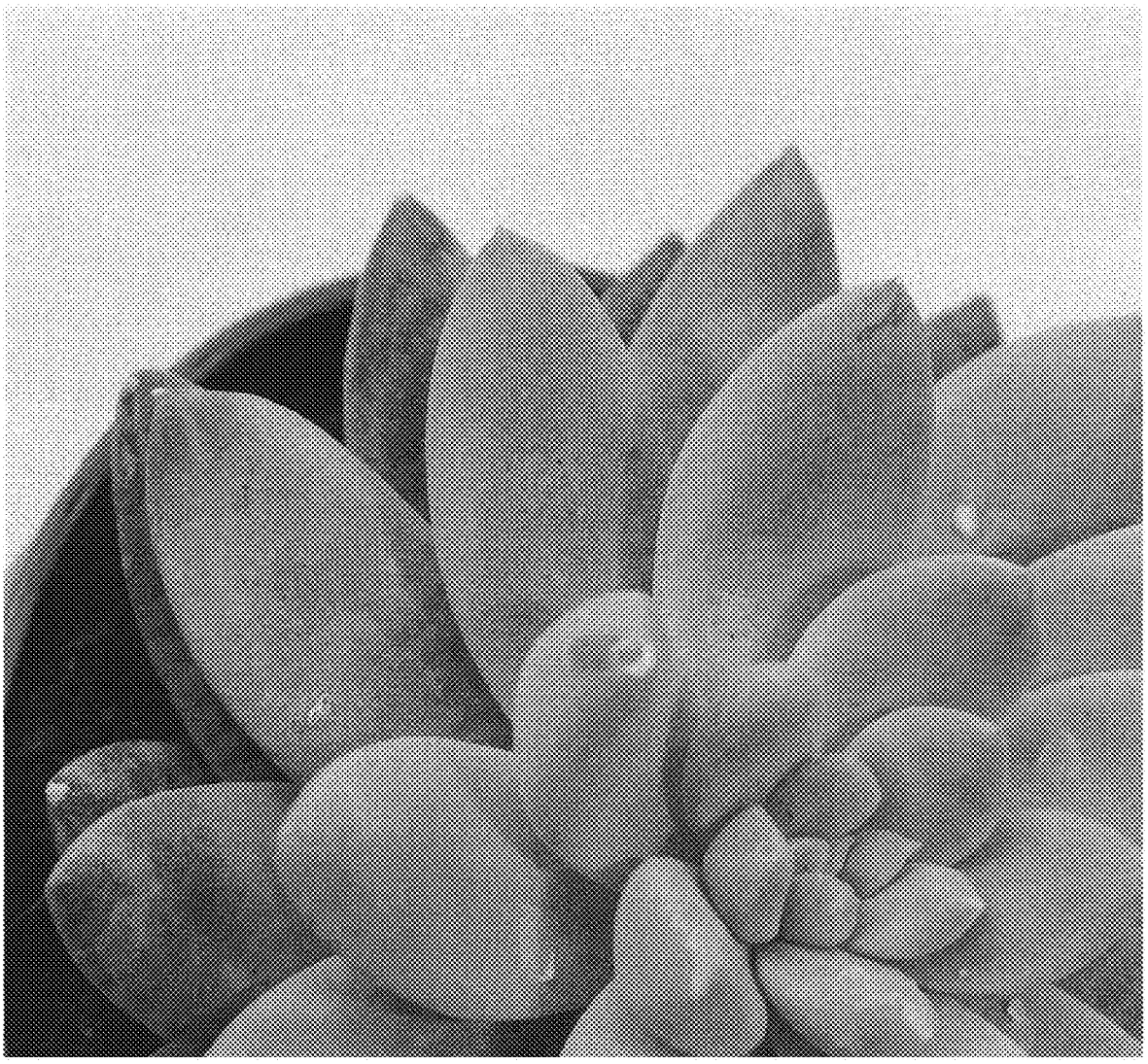
FIG. 3 illustrates, as nearly true as it is reasonably possible to make the same in color photographs of this type, the adaxial surface of the juvenile and mature foliage of 'TSAECH1802'.
Figure 4:
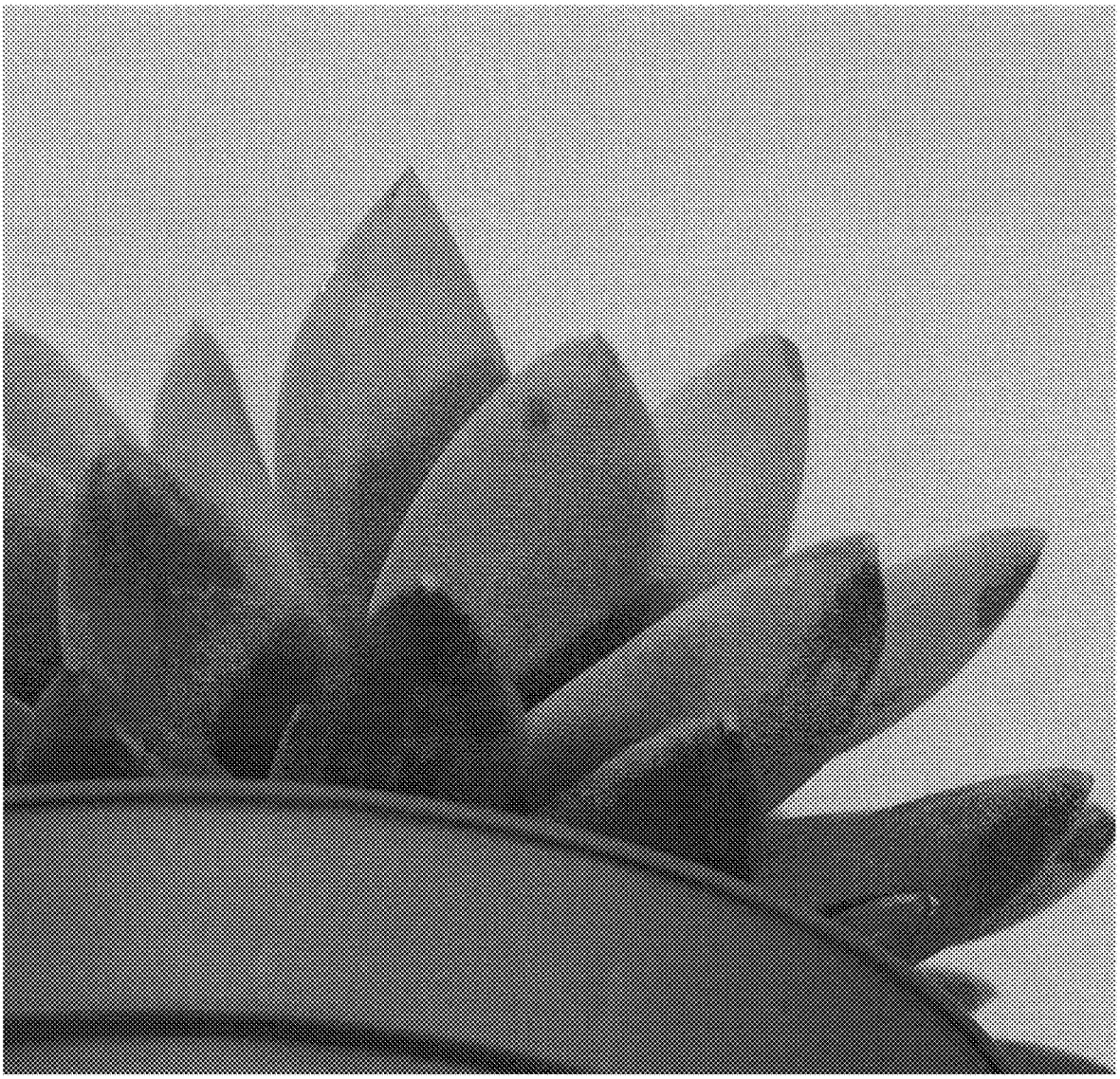
FIG. 4 illustrates, as nearly true as it is reasonably possible to make the same in color photographs of this type, the abaxial surface of the mature foliage of 'TSAECH1802'.

The following observations and measurements made in December of 2018 describe averages from a sample set of six specimens of 6 months old 'TSAECH1802' plants grown in 6 cm nursery containers at commercial greenhouse in Heerhugowaard, the Netherlands. Plants were produced using conventional greenhouse production protocols for *Echeveria* and *Sedum* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'TSAECH1802' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'TSAECH1802' and comparisons with the parent plants and closest known comparator are provided below.

Plant description:

*Growth habit.*—Succulent perennial with foliage growing in a non-branched basal rosette, eventually forming a short, unbranched stem with age.

*Plant shape.*—Flattened globular.

*Height from soil level to top of foliar plane.*—3.3 cm.

*Plant spread.*—Average of 6.4 cm.

*Growth rate.*—Slow.

*Plant vigor.*—Moderately vigorous.

*Propagation.*—Type — Leaf cuttings. Time to initiate rooting — Approximately 21 days at 18 degrees Celsius. Crop time — Approximately 20 weeks to produce a marketable plant in a 6 cm container.

*Disease and pest resistance or susceptibility.*—Neither resistance nor susceptibility to typical *Echeveria* and *Sedum* pests and diseases has been observed.

*Environmental tolerances.*—Adapt to, at least, USDA Zones 10 to 12 and temperatures as high as 40 degrees Celsius; moderate tolerance to rain yet drought tolerant once established; high tolerance to wind.

Root system:

*General.*—Fine, well-branched fibrous roots.

Stems:

*Branching habit.*—Leaves in a basal rosettes, eventually forming a short, unbranched stem with age; no lateral branching.

*Quantity of main stems.*—1.

*Main stem dimensions.*—4.3 cm long and 1.4 cm in diameter.

*Internode length.*—0.15 cm.

*Cross section.*—Rounded.

*Attitude.*—Nearly vertical.

*Strength.*—Moderately strong.

*Texture and luster.*—Glabrous and matte, due to a waxy layer covering the stem.

*Color, when developing.*—Greyed-green, nearest to RHS 194C, and covered with a waxy layer which is colored greyed-green, nearest to RHS 193D.

*Color of mature stem.*—Greyed-green, nearest to RHS 194C, and covered with a waxy layer which is colored greyed-green, nearest to RHS 193D.

*Color at internodes.*—Greyed-green, nearest to RHS 194C, and covered with a waxy layer which is colored greyed-green, nearest to RHS 193D.

Foliage:

*Arrangement.*—Rosette.

*Division.*—Simple.

*Attachment.*—Sessile.

*Quantity.*—Approximately 38 leaves per rosette.

*Shape.*—Elliptic.

*Dimensions.*—3.0 cm long, 1.2 cm wide, and 0.6 cm thick, on average.

*Aspect.*—Slightly concave and slightly curved upward.

*Attitude.*—Younger foliage near the center of the rosette is held upright and the foliage becomes progressively more relaxed towards the outer whorls of the rosette.

*Apex.*—Acute.

*Base.*—Cuneate.

*Margin.*—Entire; not undulated or lobed.

*Pubescence, texture and luster of the adaxial surface.*—Glabrous, smooth, and matte; moderately glaucous.

*Pubescence, texture and luster of the abaxial surface.*—Glabrous, smooth, and matte; moderately glaucous.

*Color.*—Juvenile foliage, adaxial surface — Greyed-green, nearest to a mixture of RHS 191A and 191B, and fading lighter towards the base, nearest to RHS 192D; the epicuticular glaucous wax covering the leaf surface is greyed-green, nearest to RHS 188B. Juvenile foliage, abaxial surface — Greyed-green, nearest to RHS 191B, and fading lighter towards the base, nearest to RHS 192D; the epicuticular glaucous wax covering the leaf surface is greyed-green, nearest to RHS 188B. Mature foliage, adaxial surface — Yellow-green, nearest to RHS 147B, and fading to a mixture of a lighter shade of yellow-green and greyed-green towards the base, RHS 147D and 192B; the epicuticular glaucous wax covering the leaf surface is greyed-green, nearest to RHS 188B. Mature foliage, abaxial surface — Yellow-green, nearest to in between RHS 147B and 147C, and fading lighter towards the base, nearest to RHS 147C; the epicuticular glaucous wax covering the leaf surface is greyed-green, nearest to RHS 188B.

*Venation.*—No venation is visible.

*Petiole.*—No petiole; leaves are sessile.

Inflorescence: No flowering has been observed to date.

COMPARISONS WITH THE PARENT PLANT AND CLOSEST KNOWN COMPARATOR

Plants of the new cultivar 'TSAECH1802' differ from the seed parent, an unnamed *Echeveria elegans* plant (not patented), in the following characteristics described in Table 1 below.

TABLE 1

| Characteristic | 'TSAECH1802' | Seed parent |
|---|---|---|
| Plant vigor. | More vigorous than the seed parent. | Weaker than 'TSAECH1802'. |
| Plant form. | Flattened globular. | Globular. |
| Foliage width. | Thicker and more rounded than the seed parent. | Thinner and more flattened than 'TSAECH1802'. |
| General coloration of the mature foliage. | Greyed-green with a bluish hue. | Appearing as a light blue-grey and heavily suffused with lilac. |

Plants of the new cultivar 'TSAECH1802' differ from the pollen parent, an unnamed *Sedum morganianum* plant (not patented), in the following characteristics described in Table 2 below.

TABLE 2

| Characteristic | 'TSAECH1802' | Pollen parent |
|---|---|---|
| Stem strength and attitude. | Moderately strong; foliage rosette is held upright on the stem. | Weaker than 'TSAECH1802'; rosette can weigh down the stem, causing it to lay flat on the ground. |
| Foliage strength at the point of attachment. | Stronger than the pollen parent; more strongly held to the stem. | More weakly held to the stem. |

COMPARISONS WITH THE CLOSEST KNOWN COMPARATOR

Plants of the new cultivar 'TSAECH1802' differ from the closest known commercial comparator, the common form of *Echeveria hookerii* (not patented), in the following characteristics described in Table 3 below.

TABLE 3

| Characteristic | 'TSAECH1802' | *Echeveria hookerii* |
|---|---|---|
| Foliage abundance. | More abundant. | Less abundant. |
| Foliage length. | Shorter than *Echeveria hookerii* | Longer than 'TSAECH1802'. |
| General coloration of the mature foliage. | Greyed-green with a bluish hue. | Blue-gray. |

That which is claimed is:

1. A new and distinct variety of x*Sedeveria* plant named 'TSAECH1802', substantially as described and illustrated herein.

* * * * *